(12) United States Patent
Salerno et al.

(10) Patent No.: US 10,830,778 B2
(45) Date of Patent: Nov. 10, 2020

(54) SLOPE SPECTROSCOPY STANDARDS

(71) Applicant: C Technologies, Inc., Bridgewater, NJ (US)

(72) Inventors: Mark Salerno, Cranford, NJ (US); I-Tsung Shih, Basking Ridge, NJ (US); Craig Harrison, Basking Ridge, NJ (US)

(73) Assignee: C Technologies, Inc., Bridgewater, NJ (US)

( * ) Notice: Subject to any disclaimer, the term of this patent is extended or adjusted under 35 U.S.C. 154(b) by 0 days.

(21) Appl. No.: 16/445,414

(22) Filed: Jun. 19, 2019

(65) Prior Publication Data

US 2019/0391168 A1    Dec. 26, 2019

Related U.S. Application Data

(60) Provisional application No. 62/762,891, filed on May 24, 2018.

(51) Int. Cl.
*G01J 3/42* (2006.01)
*G01N 33/92* (2006.01)
*G01N 21/25* (2006.01)
*G01N 33/94* (2006.01)
*G01N 21/31* (2006.01)

(52) U.S. Cl.
CPC .......... *G01N 33/92* (2013.01); *G01N 21/255* (2013.01); *G01N 21/31* (2013.01); *G01N 33/94* (2013.01); *G01N 2021/3129* (2013.01); *G01N 2201/1293* (2013.01)

(58) Field of Classification Search
CPC ........ G01J 3/02; G01J 3/42; G01J 3/28; G01J 2003/2866; G01N 21/274
USPC ......................................................... 356/319
See application file for complete search history.

(56) References Cited

U.S. PATENT DOCUMENTS

2010/0045969 A1*  2/2010  Busch .................... G01N 21/65
                                                                     356/51
2016/0011099 A1*  1/2016  Shih ..................... G01N 21/255
                                                                    356/413

* cited by examiner

*Primary Examiner* — Md M Rahman
(74) *Attorney, Agent, or Firm* — G. Kenneth Smith

(57) ABSTRACT

The present invention relates generally to a slope spectroscopy standards and methods of making slope spectroscopy standards, specifically standards and methods of developing standards specifically for variable pathlength (slope) measurements.

7 Claims, 1 Drawing Sheet

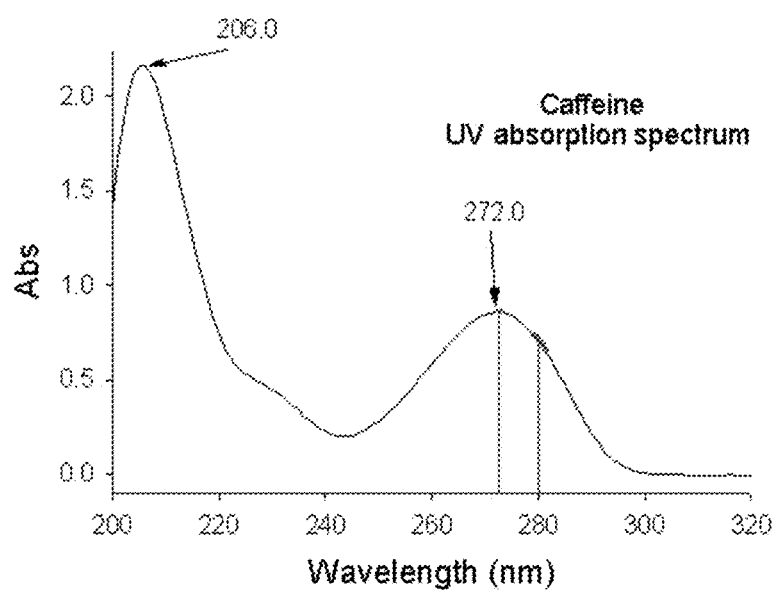

SLOPE SPECTROSCOPY STANDARDS

RELATED APPLICATIONS

This application claims priority to U.S. Ser. No. 62/762,891 which was filed on May 24, 2018.

FIELD OF THE INVENTION

The present invention relates generally to a slope spectroscopy standards and methods of making slope spectroscopy standards, specifically standards and methods of developing standards specifically for variable path length (slope) measurements.

BACKGROUND OF THE INVENTION

Spectroscopic analysis is a broad field in which the composition and properties of a material in any phase, gas, liquid, solid, are determined from the electromagnetic spectra arising from the interaction (eg. absorption, luminescence, or emission) with energy. One aspect of spectrochemical analysis, known as spectroscopy, involves interaction of radiant energy with the material of interest. The particular methods used to study such matter-radiation interactions define many sub-fields of spectroscopy. One field in particular is known as absorption spectroscopy, in which the optical absorption spectra of liquid substances are measured. The absorption spectrum is the distribution of light attenuation (due to absorbance) as a function of light wavelength. In a simple spectrophotometer the sample substance which is to be studied is placed in a transparent container, also known as a cuvette or sample cell. Electromagnetic radiation (light) of a known wavelength, $\lambda$, (ie. ultraviolet, infrared, visible, etc.) and intensity I is incident on one side of the cuvette. A detector, which measures the intensity of the exiting light, I is placed on the opposite side of the cuvette. The length that the light propagates through the sample is the distance d. Most standard UV/visible spectrophotometers utilize standard cuvettes which have 1 cm path lengths and normally hold 50 to 2000 µL of sample. For a sample consisting of a single homogeneous substance with a concentration c, the light transmitted through the sample will follow a relationship know as Beer's Law: $A=\varepsilon c l$ where A is the absorbance (also known as the optical density (OD) of the sample at wavelength $\lambda$ where OD=the $-\log$ of the ratio of transmitted light to the incident light), $\varepsilon$ is the absorptivity or extinction coefficient (normally at constant at a given wavelength), c is the concentration of the sample and l is the path length of light through the sample.

Spectroscopic measurements of solutions are widely used in various fields. Often the compound of interest in solution is highly concentrated. For example, certain biological samples, such as proteins, DNA or RNA are often isolated in concentrations that fall outside the linear range of the spectrophotometer when absorbance is measured. Therefore, dilution of the sample is often required to measure an absorbance value that falls within the linear range of the instrument. Frequently multiple dilutions of the sample are required which leads to both dilution errors and the removal of the sample diluted for any downstream application. It is, therefore, desirable to take existing samples with no knowledge of the possible concentration and measure the absorption of these samples without dilution.

Multiple sample cuvettes may solve the problem of repetitive sampling, however, this approach still requires the preparation of multiple sample cuvettes and removes some sample from further use. Furthermore, in most spectrophotometers the path length, l, is fixed.

Another approach to the dilution problem is to reduce the path length in making the absorbance measurement. By reducing the measurement path length, the sample volume can be reduced. Reduction of the path length also decreases the measured absorption proportionally to the path length decrease. For example, a reduction of path length from the standard 1 cm to a path length of 0.2 mm provides a virtual fifty-fold dilution. Therefore, the absorbance of more highly concentrated samples can be measure within the linear range of the instrument if the path length of the light travelling through the sample is decreased. There are several companies that manufacture cuvettes that while maintaining the 1 $cm^2$ dimension of standard cuvettes decrease the path length through the sample by decreasing the interior volume. By decreasing the interior volume less sample is required and a more concentrated sample can be measured within the linear range of most standard spectrophotometers. While these low volume cuvettes enable the measurement of more concentrated samples the path length within these cuvettes is still fixed. If the sample concentration falls outside the linear range of the spectrophotometer the sample still may need to be diluted or another cuvette with an even smaller path length may be required before an accurate absorbance reading can be made.

While some of these instruments provide the capability of varying the path length for measurement of highly concentrated low volume samples the applications described therein relate primarily to single path length and single wavelength measurements. Several of the instruments provide a limited number of path lengths and all are limited to path length larger than 0.2 mm. Furthermore, the devices and methods of the prior art do not provide for expanding the dynamic range of the spectrophotometer so that it is not necessary to adjust the concentration of the sample to fall within the linear range of absorbance detection of the instrument. To the extent that the prior art teaches shorter path lengths to determine the concentration of very concentrated samples or low volume samples the focus of these devices is to take a single absorbance reading at a single path length. As such the prior art references require that the path length be known with great accuracy so that an accurate concentration measurement can be made.

Historically, various liquid standard solutions have been used as accurate absorbance standards, the most common of these being potassium dichromate in various media. For example, one standard that has been used is 57.0 to 63.0 mg of potassium dichromate in 0.005M sulphuric acid dilute to 1000 ml to test absorbance at 235, 257, 313 and 350 nm wavelengths. A tenfold more concentrated solution of potassium dichromate has been used to provide an additional test point at 430 nm. The 1%/1 cm value is recorded and checked against the target range. Other solutions such as nictonic acid in 0.1M hydrochloric acid have been used to assess photometric accuracy in the far UV region. In recent years these solutions have been replaced by the use of neutral density glass filters which may be calibrated and traced to internationally recognized standards such as the National Institute of Standards and Technology (NIST).

A slope spectrometer, such as the SoloVPE™ and the Slope Spectroscopy™ provides devices and methods that provide a variable path length spectrophotometer which dynamically adapts parameters in response to real time measurements via software control to expand the dynamic range of a conventionally spectrophotometer such that samples of almost any concentration can be measured without dilution or concentration of the original sample. Using existing UV Vis Standards for the testing and qualification of slope spectroscopy systems is not an ideal situation as these standards were designed for absorbance not slope measurements. If the conventional standard is designed to be measured at a 1 mm pathlength the slope value should effectively be the certified absorbance value, but these are fundamentally different measurements, on different pieces of equipment. As such the uncertainties reported on the certificates for exiting UV Vis Absorbance Standards are not truly transferable to the slope based technology. Thus, the present invention relates to standards and methods of developing standards specifically for variable pathlength (slope) measurements.

SUMMARY OF THE INVENTION

The present invention relates to methods making a slope spectroscopy standard for a compound by selecting a compound of interest and determining the compound slope at a predetermined concentration and then determining a concentration of a second compound which corresponds to the compound of interest slope by using variable path length spectroscopy and then making a standard from the second with the slope that corresponds to the compound of interest at that particular concentration.

The present invention also relates to methods of making slope spectroscopy standards for a combination of compounds that have a particular ratio of one compound and another compound in a combination of compounds by determining the ratio of the two compounds in the combination of the compounds and determining a concentration of first substance which absorbs light at a wavelength corresponding to the first compound corresponding to the first compound by using variable path length spectroscopy and determining a concentration of a second substance which absorbs light at a wavelength corresponding to the second compound corresponding to the second compound slope by using variable path length spectroscopy and making a first substance/second substance standard by combining the first substance at a concentration with the slope corresponding to the first compound with the second substance at a concentration with the slope corresponding to the second compound at a ratio corresponding to the first compound/second combination.

The present invention relates to methods of making a slope spectroscopy standard for an antibody/drug combination of a particular ratio of drug to antibody by determining the antibody to drug ratio of the antibody/drug combination and determining a concentration of caffeine corresponding to the antibody by using variable path length spectroscopy and determining a concentration of a compound which absorbs light at a wavelength corresponding to the drug corresponding to the drug slope by using variable path length spectroscopy and making a caffeine/compound standard by combining the caffeine at a concentration with the slope corresponding to the antibody with the compound at a concentration with the slope corresponding to the drug at a ratio corresponding to the antibody/drug combination. The compound can be a colorant which absorbs light at a wavelength corresponding to the drug or the compound can be a microbead which absorbs light at a wavelength corresponding to the drug.

The present invention also relates to methods for determining the state of fitness of a spectrophotometer by testing the spectrophotometer using a caffeine standard and measuring the slope using variable path length spectroscopy and then making adjustments to the spectrophotometer and retesting the spectrophotometer using a caffeine standard and measuring the slope using variable path length spectroscopy and comparing the results of the test with the re-test to determine the state of fitness of the spectrophotometer.

FIGURES

FIG. 1 is an absorbance spectrum for caffeine.

DETAILED DESCRIPTION OF THE INVENTION

The present invention relates to standards that are used in devices and methods for determining the spectrophotometric characteristics of a solution by the use of a variable path length. For example, in determining the concentration of a compound in solution the absorbance of the solution can be determined at various path lengths. The values of the absorbance at various path lengths can then be used to calculate the concentration of the compound in the solution which are particularly useful for determining the concentration of highly concentrated samples without resorting to single or multiple dilutions of the samples. In essence these devices and methods expand the dynamic range of a standard spectrophotometer by permitting a wide range of path lengths for measuring the absorbance values of a solution. This broad dynamic range enables users to determine the concentrations of their samples without altering (diluting or concentrating) the samples. Variable path length devices may comprise a probe tip, sample vessel, motor, delivery optical fiber, detector, unidirectional sliding mechanism and appropriate software for path length control and measurement parameters.

The variable path length device may be used to measure the concentration of a sample by placing the solution sample to be tested in a sample vessel such as but not limited to a cuvette and determining the absorbance at a predetermined wavelength corresponding to the sample solution at a predetermined path length and repeating the absorbance measurement at different path lengths. Once a number of absorbance values are obtained at different path lengths a regression line can be generated from the absorbance and path length such that a slope of the regression line is obtained and the concentration of the sample may be obtained by dividing the slope of the regression line by the extinction coefficient of the sample.

Previously existing UV Vis Standards was used for the testing and qualification of these variable path length systems that utilized slope spectroscopy. However, these standards were not ideal as the UV Vis Standards were designed for absorbance measurements and not slope measurements. If a UV Vis standard is designed to be measured at a 1 mm path length the slope value should effectively be the certified absorbance value, but absorbance measurements and slope measurements are fundamentally different measurements that are determined using different pieces of equipment. As such the uncertainties reported on the certificates for US Vis standards are not truly transferable to the slope based technology. Therefore, it became necessary to develop standards specifically designed for variable path length (slope) measurements.

The standards of the present invention may be any compound that when measured at a given wavelength, create a change in absorbance at different path lengths and for which a slope can be generated. One example is caffeine which may be used as a standard for samples that absorb in the range of 280 nm, such as proteins. Other examples of compounds that can be as standards include but are not limited to NaCl which may be used to calibrate standards for salt water; KHP which may be used with water to check the pH of solutions; KCl which may be used as a salt for conductivity measurements; and KCr2O4 which is a standard for UV/Vis instruments In selecting an appropriate standard for a given compound it is desirable that the standard is sufficiently soluble or at least in the case of suspensions homogeneous in the given solution such that a measurable slope may be obtained. In the standards of the present invention the slope measured should be at least 0.01 abs/mm or at least 0.1 abs/mm or at least 0.5 abs/mm or at least 1.0 abs/mm or at least 5.0 abs/mm or at least 10.0 abs/mm or at least 25.0 abs/mm or at least 50.0 abs/mm or at least 100 abs/mm or at least 150 abs/mm or at least 200 abs/mm or at least 250 abs/mm or at least 300 abs/mm or at least 350 abs/mm or at least 400 abs/mm. In the standards of the present invention the slope measured should be from about 0.01 abs/mm to about 400 abs/mm, or from about 0.01 abs/mm to about 300 abs/mm or from about 0.01 abs/mm to about 200 abs/mm or from about 0.01 abs/mm to about 100 abs/mm or from about 0.01 abs/mm to about 50 abs/mm or from about 0.01 abs/mm to about 25.0 abs/mm or from about 0.01 abs/mm to about 10 abs/mm or from about 0.01 abs/mm to about 5 abs/mm or from about 0.1 abs/mm to about 400 abs/mm, or from about 0.1 abs/mm to about 300 abs/mm or from about 0.1 abs/mm to about 200 abs/mm or from about 0.1 abs/mm to about 100 abs/mm or from about 0.1 abs/mm to about 50 abs/mm or from about 0.1 abs/mm to about 25.0 abs/mm or from about 0.1 abs/mm to about 10 abs/mm or from about 0.1 abs/mm to about 5 abs/mm or from about 1 abs/mm to about 400 abs/mm, or from about 1 abs/mm to about 300 abs/mm or from about 1 abs/mm to about 200 abs/mm or from about 1 abs/mm to about 100 abs/mm or from about 1 abs/mm to about 50 abs/mm or from about 1 abs/mm to about 25.0 abs/mm or from about 1 abs/mm to about 10 abs/mm or from about 1 abs/mm to about 5 abs/mm or from about 5 abs/mm to about 400 abs/mm, or from about 5 abs/mm to about 300 abs/mm or from about 5 abs/mm to about 200 abs/mm or from about 5 abs/mm to about 100 abs/mm or from about 5 abs/mm to about 50 abs/mm or from about 5 abs/mm to about 25.0 abs/mm or from about 5 abs/mm to about 10 abs/mm or from about 10 abs/mm to about 400 abs/mm, or from about 10 abs/mm to about 300 abs/mm or from about 10 abs/mm to about 200 abs/mm or from about 10 abs/mm to about 100 abs/mm or from about 10 abs/mm to about 50 abs/mm or from about 10 abs/mm to about 25.0 abs/mm. In preferred embodiments of the standards of the present invention the standard does not substantially degrade over time such that the slope measurement is constant over time. In some embodiments of the standards of the present invention, the standard in a "sealed" condition may have a shelf life of 3 months or more, or 6 months or more or 1 year or more or 2 years or more or 5 years or more. The working life of the standard should also have a useful life while being used during a test, such that there is little degradation over a span of ten minutes or more. The standard solution should be stable over the time it takes to use the solution. Since the standard may be water based it may start to evaporate and thus change over time if left exposed to the environment.

One example of a slope spectroscopy standard of the present invention is caffeine in water as it provides a user-friendly material with excellent stability, great solubility and customization across a range of slope values. In one embodiment of the standards of the present invention a stock solution of roughly 10,000 ppm or 10 mg/ml concentration of pure caffeine in water is made. From that stock the caffeine solution is diluted to a predetermined target range that corresponds either to a predetermined standard slope or a custom standard slope that is created based on a particular compound or on a multi-component product such as an antibody drug conjugate. The standards of the present invention provide a certified slope value with an uncertainty that is NIST traceable. This is done in accordance with ISO 9001:2008 Quality Management System and in compliance with the ISO 17025:2005 and ISO Guide 24:2009 standards. The measurement and certification is based upon a version of variable path length technology that has closed loop control of the path length and high resolution.

In pharmaceutical and biological processes the concentration of substances including that active pharmaceutical compound or biological substance within fluid samples may be measured intermittently or continuously during and after processing or purification of the compound of interest. It is of great interest to know with great precision and accuracy the concentration of any given substance at any time in the process. It is especially important to be able to quantify the final product of a process especially when that product is being sold to the public for treatment of diseases. Having a standard that ensures that the concentration of the solution, as measured by the spectrophotometric instrument, is an essential part of good quality management.

With any standard there is a certain level of uncertainty. The source of that uncertainty may be related to a variety of factors including the instrument used, homogeneity of the sample, the variation of the sample vessel and other factors. Obviously, the better the instrument for measuring the sample and the more homogenous the sample, the lower the uncertainty of the measurement. Often, when reporting uncertainty the values, are usually reported in the context of the instrument which means the assumption is that the uncertainty value is the same for all instruments. This approach is simplistic and inaccurate. For example there can be a standard with a reported uncertainty value of <1% uncertainty but on a high-end instrument. This value will not be the same on a lesser instrument. Furthermore, the uncertainty likely varies with varying slope numbers. A lower slope value will have larger step changes and probably less error, while a larger slope value will have small step changes and therefore a larger error. The standards of the present invention may be used at a particular wavelength at which the standard absorbs light or can be used at a wavelength near where the standard absorbs light. The uncertainty increases as the wavelength used is further from the optimum absorbance wavelength.

Measured Slope vs. Certified Slope Value:

The Certified Slope Value is determined by a statistically based uncertainty determination method and takes into account a number of variables (controlled and uncontrolled). The value is typically expressed with a 95% confidence. When using the Slope Standard a comparison is made between the measured slope and the certified slope value. If the measured value(s) do not fall within a range that is set by combining the uncertainty of the standard and the slope uncertainty of the instrument being evaluated, and all other sources of potential variation (e.g. cleanliness, method, handling etc.) have been ruled out, the system is likely not performing as intended.

Standard Deviation of the Measured Slope Values (1→n):

Standard deviation or other statistical techniques (e.g. RMS, MSD, analysis of residuals, etc.) may be used to evaluate the repeatability of multiple measurements and the spread of the data. Using a known sample with a certified slope value serves as an excellent benchmark for assessing the repeatability performance of the system which has a known value. Depending on the spectroscopic device being evaluated that value could range from ±1 to ±5. The benefit of the standard is having a sample of known performance and stability so performance can be determined with higher confidence. The actual threshold value used that may be used to diagnose an issue can vary depending on the device potentially the nominal slope value of the standard itself. These statistical methods are a way of determining the ariability between slope measurements.

Linearity Results (Strength of Correlation) $R^2$:

While the standard deviation of the measure slope values is a metric for determining the variability between slope measurements, linearity results look at performance variability within a single measurements based upon multiple absorbance values at different path lengths. Using a known standard with a known method should provide a highly predictable result based upon the capability of the instrument being assessed. A poor correlation, represented by low $R^2$ values, may indicate an issue with the system. Typically methods are developed to deliver a minimum $R^2$ value of 0.999 with a minimum number of data points. The exact method used with each standard may be based upon method development and validation work for the various slope values being produced. Linearity deviations can indicate multiple issues that may involve photometric issues with the system or potentially the motion control of the system. Sometime cleanliness of the system is the issue. With linearity the R2 value and data point count will need to meet some minimum level of expectations. If non-linear points appear or need to be excluded, which is atypical for the method, there is likely a problem.

Absorbance Range (Min/Max Values):

While the photometric range of the spectrophotometer engine is set, issues of optical coupling, lamp age, cleanliness and alignment can all influence the amount of light transmitted through the system. While this value may be unique for each system, it should generally fall within a certain predicatable range. The absorbance result for a given standard is could indicate whether there is more or less light than would be expected for a given slope value (concentration). It is more probable that less light is traversing the path length which will indicate a problem, however, the possibility of too much light could reveal a stray light issue.

In the most basic example of the standards of the present invention, a predetermined concentration of a standard can be analyzed by variable path length spectroscopy to determine the slope of that concentration as described above. In one embodiment of the methods of the present invention serial dilutions of the compound chosen for the standard can be used to create a standard curve of slopes "book ending" the range of slopes. This step may be accomplished using a robotic system set up for diluting. From this data a concentration can be chosen for a desired slope. The tolerance for the desired slope can be determined. It is important that whether the predetermined slope is 5 and the standard is 4.9, that the standard 4.9 is NIST traceable.

The uncertainty for any given standard should be less than 10% or less than 9% or less than 8% or less than 7% or less than 6% or less than 5% or less than 4% or less than 3% or less than 2% or less than 1.5% or less than 1.4% or less than 1.3% or less than 1.2% or less than 1.1% or less than 1.0% or less than 0.9% or less than 0.8% or less than 0.7% or less than 0.6% or less than 0.5% or less than 0.4% or less than 0.3% or less than 0.2% or less than 0.1%. The uncertainty for any given standard should be between about 0.05% to about 10% or from about 0.05% to about 9% or from about 0.05% to about 8% or from about 0.05% to about 7% or from about 0.05% to about 6% or from about 0.05% to about 5% or from about 0.05% to about 4% or from about 0.05% to about 3% or from about 0.05% to about 2% or from about 0.05% to about 1.5% or from about 0.05% to about 1.4% or from about 0.05% to about 1.3% or from about 0.05% to about 1.2% or from about 0.05% to about 1.1% or from about 0.05% to about 1.0% or from about 0.05% to about 0.9% or from about 0.05% to about 0.8% or from about 0.05% to about 0.7% or from about 0.05% to about 0.6% or from about 0.05% to about 0.5% or from about 0.05% to about 0.4% or from about 0.05% to about 0.3% or from about 0.05% to about 0.2% or from about 0.05% to about 0.1% or from about 0.1% to about 10% or from about 0.1% to about 9% or from about 0.1% to about 8% or from about 0.1% to about 7% or from about 0.1% to about 6% or from about 0.1% to about 5% or from about 0.1% to about 4% or from about 0.1% to about 3% or from about 0.1% to about 2% or from about 0.1% to about 1.5% or from about 0.1% to about 1.4% or from about 0.1% to about 1.3% or from about 0.1% to about 1.2% or from about 0.1% to about 1.1% or from about 0.1% to about 1.0% or from about 0.1% to about 0.9% or from about 0.1% to about 0.8% or from about 0.1% to about 0.7% or from about 0.1% to about 0.6% or from about 0.1% to about 0.5% or from about 0.1% to about 0.4% or from about 0.1% to about 0.3% or from about 0.1% to about 0.2% or from about 0.5% to about 10% or from about 0.5% to about 9% or from about 0.5% to about 8% or from about 0.5% to about 7% or from about 0.5% to about 6% or from about 0.5% to about 5% or from about 0.5% to about 4% or from about 0.5% to about 3% or from about 0.5% to about 2% or from about 0.5% to about 1.5% or from about 0.5% to about 1% or from about 1% to about 10% or from about 1% to about 9% or from about 1% to about 8% or from about 1% to about 7% or from about 1% to about 6% or from about 1% to about 5% or from about 1% to about 4% or from about 1% to about 3% or from about 1% to about 2% or from about 2% to about 10% or from about 2% to about 9% or from about 2% to about 8% or from about 2% to about 7% or from about 2% to about 6% or from about 2% to about 5% or from about 2% to about 4% or from about 2% to about 3% or from about 3% to about 10% or from about 3% to about 9% or from about 3% to about 8% or from about 3% to about 7% or from about 3% to about 6% or from about 3% to about 4%.

In other embodiments of the present invention a standard for the slope for a particular compound of interest at a particular concentration may be developed by determining the concentration of a standard which provides the identical slope value to that of particular compound of interest at the particular concentration. For example, it may be desirable to have a standard which mimics the slope of a commercial drug compound at the concentration of the drug in the final product. Having the standard for that particular drug at that particular concentration can provide a release test for that drug as long as the drug is within the error range of the desired concentration.

In other embodiments of the present invention a standard for the slopes of a particular combination of compounds such as antibody drug conjugates is desirable. Antibody-drug conjugates or ADCs are highly potent biopharmaceutical drugs designed as targeted drug therapy for the treatment of people with cancer. ADCs are complex molecules composed of an antibody linked, via a stable, chemical linker with labile bonds, to a biological active cytotoxic compound. The manufacture of ADCs provides the challenge of conjugating the cytotoxic drug component to the antibody via a chemical linker in a reproducible fashion. It is desirable to characterize the drug to antibody ratio, the amount of bound drug versus unbound drug, the amount of unbound linker and to determine the stability of the ADC both in vitro and in vivo. For these compounds a primary goal is to ensure that the ratio of drug to antibody falls within a targeted range. To mimic the antibody-drug combination the standards of the present invention may use a combination of a materials such as caffeine and a compound that absorbs light at a wavelength similar to a drug. Such a compound may be but is not limited to a stable colorant, micro-beads or off peak absorber of another type to allow variable path length users to have a certified drug:antibody ratio that can be measured for qualification and system suitability.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

A better understanding of the present invention and of its many advantages will be had from the following examples, given by way of illustration.

We claim:

1. A method of making a slope spectroscopy standard for a compound comprising:
    selecting a compound;
    determining the slope at a predetermined concentration of the compound;
    determining a concentration of a methylxanthine standard which corresponds to the compound slope by using variable path length spectroscopy wherein the compound and the standard are different compounds and wherein the compound and the standard have absorbance spectra that share a common absorbance wavelength; and
    making a standard of an appropriate concentration which provides a slope measurement that corresponds to that of the compound wherein the standard has a slope measurement of from about 0.01 to 500.

2. The method of claim 1 wherein the standard is in an aqueous solution.

3. The method of claim 1 wherein the standard has a slope measurement of from about 1 to 500.

4. The method of claim 1, wherein the methylxanthine is selected from the group consisting of caffeine, aminophylline, IBMX, paraxanthine, pentoxifylline, theobromine, and theophylline.

5. The method of claim 4 wherein the methylxanthine is caffeine.

6. The method of claim 1 wherein the standard is selected from the group consisting of NaCl, KHP, KCl and KCr2O4.

7. The slope spectroscopy standard of claim 1 wherein the standard has an uncertainty value of from about 0.1% to about 5%.

* * * * *